United States Patent [19]

Ivancic et al.

[11] Patent Number: 5,281,826
[45] Date of Patent: Jan. 25, 1994

[54] VIDEO FLUORESCENCE MONITOR FOR DETERMINATION OF SPILL OUTLINES

[75] Inventors: William A. Ivancic; Russell H. Barnes; Daniel R. Grieser, all of Columbus; Patrick J. Callahan, Lancaster, all of Ohio

[73] Assignee: Electric Power Research Institute, Inc., Palo Alto, Calif.

[21] Appl. No.: 813,112

[22] Filed: Dec. 23, 1991

[51] Int. Cl.$^5$ ............................................. G01J 1/58
[52] U.S. Cl. .............................. 250/461.1; 250/458.1; 250/459.1
[58] Field of Search ............... 250/458.1, 459.1, 461.1, 250/253

[56] References Cited

U.S. PATENT DOCUMENTS

| | | | |
|---|---|---|---|
| 3,043,908 | 7/1962 | Madsen | 250/253 X |
| 3,501,639 | 3/1970 | Monroe | 250/461.1 |
| 3,899,213 | 8/1975 | Fantasia et al. | 250/461.1 X |
| 4,200,801 | 4/1980 | Schuresko et al. | 250/458.1 |
| 4,794,260 | 12/1988 | Asano et al. | 250/458.1 |
| 5,034,615 | 7/1991 | Rios et al. | 250/461.1 |
| 5,140,416 | 8/1992 | Tinkler | 358/125 X |

FOREIGN PATENT DOCUMENTS 385205 9/1990 United Kingdom ............. 250/458.1

OTHER PUBLICATIONS

Applied Optics, vol. 18, No. 11, Jun. 1, 1979, p. 1746, "Teledetection of the Thickness of Oil Films on Polluted Water Based on the Oil Fluorescence Properties."
Applied Optics, vol. 29, No. 16, Jun. 1, 1990, p. 2392, "Fluorescence Imaging Inside an Internal Combustion Engine Using Tunable Excimer Lasers."
Applied Optics, vol. 28, No. 3, Feb. 1, 1989, p. 472, "Short- and Long-term Memory Effects in Intensified Array Detectors: Influence on Airborne Laser Fluorosensor Measurements."
Applied Spectroscopy, vol. 41, Nov. 4, 1987, p. 625, "Photodiode Array Detection in Analytical High-Resolution Molecular Luminescence Spectroscopy."
Photonics Spectra, Nov. 1989, p. 161, advertisement article "The Clear Answer to Your Toughest Imaging Applications."
Photonics Spectra, Feb. 1989, p. 132, advertisement article "The World's Most Flexible Spectral Analysis System."
Jandel Scientific, Apr. 1990, advertisement article "Java Puts Video Analysis Within Reach."
Hamamatsu Corp., 1988, advertisement article "Need to See in the Middle UV?".
Photonics Spectra, Apr. 1989, p. 98, advertisement article "New! Remote Spectral Measurement System."
Applied Optics, vol. 29, No. 22, Aug. 1, 1990, p. 3218, "Lidar Fluorosensing of Mineral Oil Spills on the Sea Surface."

Primary Examiner—Constantine Hannaher
Assistant Examiner—Edward J. Glick
Attorney, Agent, or Firm—Flehr, Hohbach, Test, Albritton & Herbert

[57] ABSTRACT

Disclosed is a real-time fluorescence imaging system for detecting on-site the presence and boundaries of spills of insulating liquids for transformers and capacitors and other fluorescing materials providing a two-dimensional image of the spill having excitement means positionable near a spill for exciting fluorescence emissions from the spill materials, image intensification means for intensifying the fluorescent emissions, first detection means positionable to detect intensified fluorescent emissions from the insulating liquids and generating a detection signal, and display means for receiving the detection signal and generating a real-time video image of the presence and boundaries of the spill. The present invention also includes pulse means for causing the excitement means to periodically excite fluorescent emissions from the insulating liquids and control means for controlling the intensification means to intensify only during periods of fluorescent excitation.

18 Claims, 3 Drawing Sheets

VIDEO FLUORESCENCE MONITOR FOR DETERMINATION OF SPILL OUTLINES

FIELD OF THE INVENTION

The present invention relates to a video fluorescence monitor. More specifically, it relates to an apparatus and method for real-time on-site video imaging for the detection of the presence and boundaries of a spill of material of fluorescent type on surfaces. PCB, PCB-contaminated mineral oil, mineral oil-based fluorescing mixtures, and mineral oil-based insulating liquids. are specifically included.

BACKGROUND OF THE INVENTION

Spills of insulating liquids for transformers and capacitors on many surfaces often cannot be seen readily by the eye. The presence and boundaries of a spill have typically been determined by applying costly and time-consuming statistical sampling procedures. Furthermore, more sampling is required for cleanup completeness inspections.

For spill clean-up efforts, sophisticated laboratory equipment is either brought to the spill site for sampling or the samples are sent to a central laboratory. In the first case, use of portable gas chromatograph requires special operator training. In the second case, the sample's trip to the laboratory takes time. Often the spill is required to be cleaned up before any analytical results can be returned from the lab resulting in costly over clean-up or missed spots.

The cleanup of spills of insulating liquids for transformers and capacitors would be better accomplished through a system which provides the ability to easily and concisely map the boundaries of a spill occurring on surfaces such as asphalt, concrete, grass and dirt and wet surfaces. Moreover, a system providing a real-time picture monitor of cleanup efforts could facilitate useful information gathering. Furthermore, a system which does not require time consuming sampling procedures during the initial cleanup inspections could provide for more efficient and thorough spill cleanup operations. Therefore, there is a need for a real-time, user friendly system for distinguishing the spill from the nonspill area.

Accordingly, in an attempt to achieve the above listed objects, a real-time monitor system has been developed which provides an operator the ability to see fluorescent emissions from a spill in order to map out its boundaries. An excitation source lamp is used to optically induce fluorescent emissions by the insulating liquids. The boundaries of the spill are mapped by placement of markers according to detected emissions made visible to a viewer on a video display monitor. The system operates so that a first and second detector generate images which may be received by a first monitor and/or second monitor.

The real-time monitor system described above experiences interference of the emission signals in that their detection is influenced by the sun's radiation. A mobile box style sun block has been used for shielding the UV radiation from the sun for daytime operation. Because a sun block shield or tent is cumbersome, the system does not allow the user to easily and quickly map the spill. Furthermore, the system of the prior art does not include means for intensifying and gating the fluorescent emissions of the spill contents necessary to avoid this solar interference.

OBJECTS AND SUMMARY OF THE INVENTION

It is therefore a general object of the present invention to provide an improved fluorescence video monitor system for distinguishing the spill from the nonspill area.

It is another object of the present invention to provide a real-time fluorescent video imaging system which may be used in the daylight.

It is also an object of the present invention to provide a system which avoids influence from the source of excitation light in the reception of the emission signals.

It is a further object to provide an excitation source which operates at wavelengths providing optimized fluorescent emissions of most insulating liquids and a detector which receives the fluorescent emission signals at their optimized wavelengths.

It is still another object to provide a system to allow the operator to better map the boundaries of a spill occurring on surfaces such as asphalt, concrete, metal, grass and dirt and wet surfaces by providing a means for distinguishing the fluorescent emissions of the spill contents from the surrounding environment.

Another object is to have at least two detectors, a first for viewing fluorescent emissions and a second for viewing the normal video image and means to switch between their transmissions at a monitor and audio input for coordination of the documentation process of the clean-up.

The foregoing and other objects of the invention are achieved by a real-time fluorescence imaging system for detecting the presence and boundaries of spills of insulating liquids for transformers and capacitors or other fluorescing materials. The system provides a two dimensional image of the spill having the excitation mean positioned near the spill for producing fluorescent emissions of the insulating liquids, image intensification means for intensifying the fluorescent emissions, first detection means positionable to detect intensified fluorescent emissions from the insulating liquids and generating a detection signal, and display means for receiving the detection signal and generating a real-time video image of the presence and boundaries of the spill. The present invention also includes pulse means for causing the excitation means to periodically excite fluorescent emissions from the insulating liquids and control means for controlling the intensification means to intensify only during periods of fluorescent excitation.

The excitation means is an optically filtered lamp bulb providing wavelengths of between approximately 190 nm to 350 nm for exciting fluorescent emissions of said insulating liquids having a roughened or smooth surface and an aluminized coating over the surface except for the transparent hole where the light is emitted. The fluorescence detection means is sensitive at wavelengths between 340 nm and 450 nm in chosen (narrow 10 nm) bands. Furthermore, the method of providing a real-time fluorescence imaging system includes the step of applying an absorbent/adsorbing powder to the area of the spill to absorb/adsorb insulating liquids from the underlying ground to concentrate the insulating liquids at the ground's surface. Also provided are switching means for allowing a viewer of the display means to view images from both a first detection means and a second detection means, the second detection means observes the overall video image of the spill area to allow correlation of the analyzed image and first detector's position and viewing area near it.

BRIEF DESCRIPTION OF THE DRAWINGS

Other objects, and many of the intended advantages of the present invention, will be readily appreciated as the same becomes better understood by reference to the following detailed description when considered in connection with the accompanying drawings wherein.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the claims.

Figure 1:
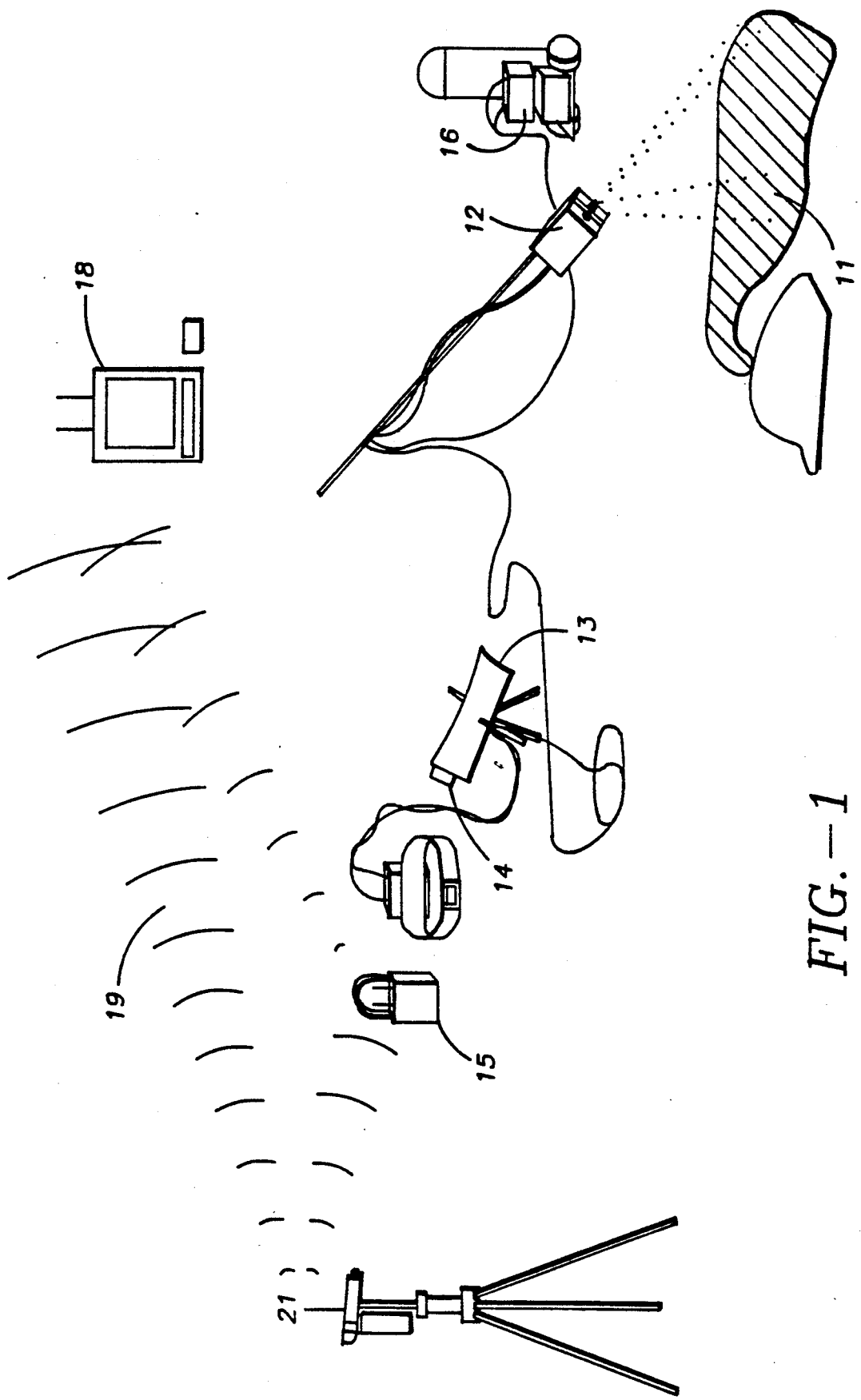
FIG. 1 shows the basic components of a fluorescent monitoring system.

Attention is drawn to FIG. 1 showing the basic components of a portable, hand carried fluorescent monitoring system. The spill 11 is illuminated by an easily positionable source lamp 12. An operator positions the detector 13 to receive fluorescent emission signals excited in the spill by lamp 12 and generates video signals. The spill 11 of insulating liquids for transformers or capacitors which are mineral oil and askarel materials (PCBs), are considered highly toxic or regulated. Such liquids include oil-based liquids and silicon-based liquids, among others. Therefore, immediate cleanup of the spill site is imperative. Other fluorescing materials such as gasoline spills or fuel oil spills may be analyzed in the same manner.

The detector 13 sends the video signals to a video monitor 14 at the back of detector 13 which is in close proximity to the operator to display the received image. The excitation source 12 and detector 13 and excitation unit may be incorporated into a single unit as shown for ease of handling. The source lamp 12 is powered by battery 16 and the detector 13 and monitor 14 are powered by a belt mounted battery 17. Belt mounted power has also been used to power the source 12.

Non-fluorescent images may be detected at a remote location by a remote second detector 21 and may be viewed on a remote second monitor 18 via RF transmissions 19. This information link can be also made by cable. Furthermore, the images from the second detector 21 may also be viewed by the operator at the first monitor 14 or directed to the VCR.

The present system allows an operator to differentiate spill areas from nonspill areas and to compare areas of lower and higher spill concentration in addition to determining the spatial extent of the spill. Under field conditions, the spill may be in thin layers, and therefore, the intensity of the fluorescence varies according to bulk thickness. Combinations of properties such as the absorption coefficient at the excitation wavelength as well as scattering properties of the background materials make a difference in the ability of the system to discriminate the spill edge.

Figure 2:
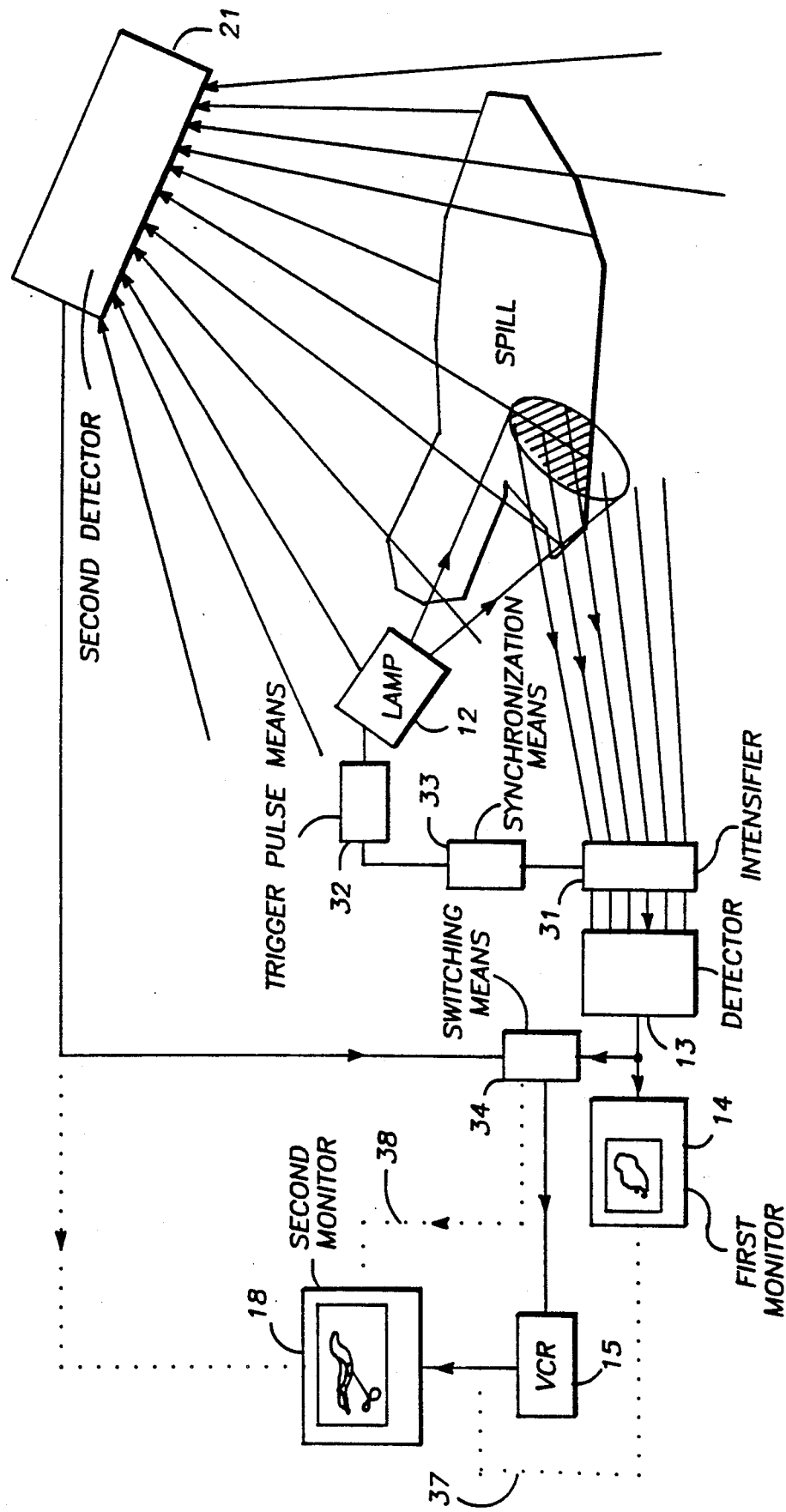
FIG. 2 is a block diagram of the present invention.

Turning to FIG. 2, the lamp source 12 provides an ultra-violet emitting optical excitation source which causes the PCB mineral oil or other spilled material to fluoresce and emit fluorescent light from the spill 11. A material fluoresces when its molecules or atoms absorb electromagnetic energy, and then re-emits this energy as electromagnetic radiation. The excitation energy used to pump up the molecule is generally at a higher electromagnetic energy, or shorter wavelength than the emitted radiation. Electromagnetic energy is inversely related to the wavelength of the light for both the excitation and the emitted wavelengths. Fluorescence is an inherently inefficient process and only a small fraction of the energy originally directed to excite the sample is emitted as fluorescence.

The lamp 12 induces optical output characteristics of the spill materials that can be detected by the optically filtered video sensor 13. The intensifier 31 added to the front of the detection sensor intensifies the signals of the fluorescence which are strong enough to be observable by the sensor alone only when the typical spill is thick. The intensifier 31 has the added property that it shifts the sensitivity farther into the UV region than the video sensor's operational range. The optical filtering eliminates much of the interfering radiation by narrowing the observation window to the wavelength of interest. The optical filtering is not complete enough in eliminating interference to the minimum levels.

To overcome the effects of additional interference, from the sun in particular, the intensifier 31 provided is a gated unit. This gating periodically limits the signal input in time so that the vast majority of the solar emissions (which are continuously present) are excluded from the detection unit. The intensifier 31 is synchronized with the source lamp 12 so that when the source flash occurs, nearly all of the fluorescent output from the spill emanates from the spill during the same time period that the gate is open. The source lamp 12 of the present invention is pulsed periodically to excite the fluorescent emissions in the spill by pulse means 32.

The gated image intensifier 31 and its synchronization with the trigger pulse means 32 of the source lamp 12 which is effected by synchronization means 33 is provided by any suitable electronic circuit configuration.

The fluorescent emission signals generated by the insulating liquid are intensified by intensifier 31 so that the signals received by a detector can readily be converted to real-time display apparatus. Intensification of the collected signal is accomplished by using a microchannel plate photon multiplication of the incidence photons to produce an image about 10,000 times stronger than the incident energy. This energy is then projected onto the sensing elements of the detector 13, which is a CCD camera or vidicon camera. The intensifier chosen for this application possesses coatings to enhance UV detection, a quartz window, and operates in gated mode for interference rejection.

The construction of the image intensified optical collection system 31 and 13 includes a 2.54 cm diameter quartz lens for collection of the radiation emitted from the sample. The optical strength of the lens is f/1.5. This strength and size are nominally optimum for projection onto an intensifier having an 18-mm cathode, while providing a convenient field of view for the operator. The high magnification properties of the f/1.5 lens allows collection of the light from a wide field of view.

This single lens lowers cost because the typical quartz camera unit uses a lens over specified in optical resolution for this application. This application only requires a low resolution image. By using a lens of 2.54 cm diameter with a f/1.5 collection, the observation area is about 1 m$^2$ in the field of view during a measurement at a convenient observation distance.

In the detection unit 13 there is also another lens. It has a small but high throughput image transfer lens and is used to direct the output of the image intensifier phosphor screen to place the image on the sensing elements. The placement and focusing properties of this lens allow the sample image to be reduced to the size of the sensing elements.

The wavelengths at which the excitation source operates depend on the light source, the optical filtering, and the material being observed. The type of the insulating liquids or other fluorescing material forming the spill is determined in the typical manner, such as checking records or by other tests. The present case, the material being observed typically comprises oil and PCBs in varying proportions. Therefore, both the oil and the PCBs must be considered in choosing the excitation wavelength. Any means for achieving the excitation wavelengths are within the scope of the present invention.

The fluorescent excitation range of mineral oil is in the range of 190 nm to about 340 nm. In PCB contaminated insulating liquids, the mineral oil is the predominantly detected component because it is carried with the PCB impurity. Maximum sensitivity for mineral oil excitation requires excitation below 280 nm, which is the condition which applies when the system operates using a mercury excitation source having an excitation wavelength of 254 nm. The same wavelength can also be obtained with other sources such as an optically filtered Xenon source.

With a very strong 254 nm line, the mercury lamp emits energy for excitation. The mercury source is a line source and needs no optical filtering. The output is sufficient for excitation of a predominantly mineral oil-based insulating liquid. Fluorescence output for mineral oil is greater for this excitation than when excited at 300 or at 325 nm which spans a range of other available mercury lines.

The sun-excluding properties of the pulsed and optically filtered xenon source make it an adequate pulsed source for the mineral oil, PCB materials, and a wide variety of other fluorescing species such as gasoline and fuel oil. The xenon source is filtered to yield maximum excitation output between 230 nm and 350 nm using a commercially available filter (Solar Blind Filter) having an 85 nm bandwidth with transmittance centered at 290 nm. A double thickness of this commercially available filter is used for a filter thickness of about 13 mm. This causes a sharper cutoff of the energy at about 325 nm rather than extending to 350 nm as in the commercial specification of the single thickness. A custom filter with similar bandwidth cutting off 10 nm lower in wavelength would be optimum.

Excitation of the PCB materials produces maximum detectability when the excitation maximum is near 300 nm. The mercury lamp having an output of 302 nm and 313 nm can be used, but these mercury lines are inherently weaker than the filtered xenon. Coatings that shift the output of the strong mercury lamp line at 254 nm to 300 nm are available but typical commercial available lamps cause interferences that lower sensitivity of the system to PCB. The xenon-pulsed source is preferred for the detection of PCB insulating materials. The commercially available filter ("Solar Blind" Filter) discussed above is used to obtain the maximum excitation with the xenon lamp near 300 nm that is necessary.

Observation wavelengths are also dependent on the optical filtering used in the excitation. The filter used is nominally 10-nm wide in transmittance. Observation is performed generally below 420 nm because of the lower presence of energy in the sun and other visible light sources, although some fluorescence energy from the mineral oil and PCBs extend above this level. Because of the blockage of interfering radiation, the pulsed xenon source system is preferable.

Observations should be in a bandwidth in the range above 325 nm but may extend over 200 nm above the excitation frequency because the mineral oils and PCB materials emit fluorescent energy in this wide band. The strongest emissions for the PCBS are at about 340 to 410 nm using excitation at 280 nm to 325 nm. For mineral oil-based systems with or without PCBS, the peak of the emission is near 350 nm, but is however still strong at 380 nm.

Observation is usually made at 350 nm for the mineral oil-based liquid when excited by the mercury source. Mercury line interference at 365 nm is avoided while detection is at the fluorescence peak. Observation bandwidth is 10 nm.

Due to the interferences of the source, observations are made at 380 nm when the xenon lamp is used for either liquid. At approximately 350 nm, the system avoids most other interferences in the environment. Optimum operation at this wavelength requires a change in the excitation filter that blocks out the energy 10 nm lower than the 330 nm, which is commercially available.

Figure 3:
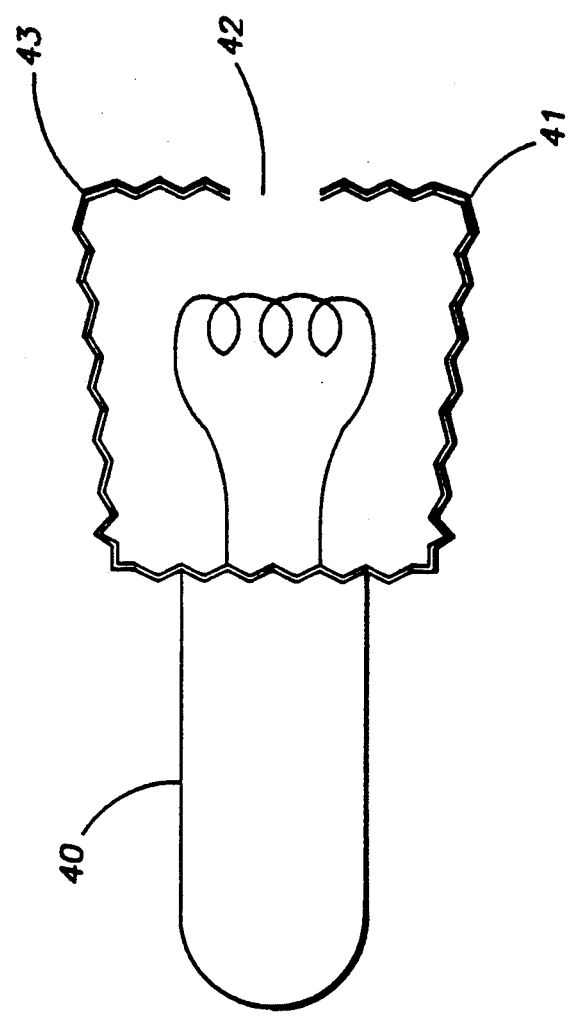
FIG. 3 shows an aluminum coated light source having an opening.

An aluminum coating 43 (as shown in FIG. 3) on the bulb 40 of the source lamp 12 enables the bulb to be operated with an increased energy output. A second improvement of the source lamp 12 consists of the surface 41 of the bulb 40 being roughened (except for the clear opening 42 of about 1.27 cm in the front of the bulb 40) before application of the aluminized coating 43. The roughening provides scattering surfaces in the aluminized surface by which the light changes directions more randomly so that the light energy leaves the bulb 40 through the nonaluminized quartz opening 42 before being absorbed by multiple reflections and transmissions.

A method for enhancement of the fluorescent emissions involves the step of applying an absorbent powder to the area of the spill to absorb insulating liquids from the underlying ground to concentrate the insulating liquids at the grounds surface. The signal from the spill is enhanced by spreading sorbent material such as dehydrated $CaSO_4$ having the ability to absorb or adsorb the PCB or the mineral oil or other insulating liquid into or onto its surfaces.

The absorbent/adsorbent powder pulls material out of its original area of deposit. Moreover, the successful material allows a certain amount of transfer of the excitation light into the interstitial areas and also allows the light to transfer out of the material because of high reflectance in the amorphous state. Furthermore, unreflected energy is transmitted into the material, not absorbed, and therefore available to interact with spill material when it is re-emitted and reflected again into the interstitial areas, allowing additional interactions in the wavelength regions that coincide with the additional PCB materials that are pulled up. The effect is that the layer of observation is spectroscopically thicker than the actual surface. Different materials having the same properties as CaSOhd 4 or different properties, including but not limited to CaO, $MgSO_4$ and AlO may also be used.

By viewing both the first detector's video image of fluorescence and the second detector's normal video image simultaneously, for example, on a split screen, the ability to map out the boundaries of the spill is enhanced because the fluorescent image can be compared with normal image to determine where in the area it was observed. By continuously monitoring clean-up efforts, the present system provides cost efficient cleanups in that extra area is not taken into the original clean-up area. Part of the methodology in this case is to observe successive layers for contamination spots as the previous layer is removed.

As described above with reference to FIG. 1, the images received by the second detector 21 for viewing the normal video image may be sent to the first monitor 14 on VCR 15 by RF transmission or by cable. Switching means 34 for allowing a viewer of the first monitor or the second monitor to view images of both the first detector 13 and the second detector 21 are provided by any suitable electronic configuration. Based on either simultaneous or back-to-back observations, the operator or a helper may plant markers around the edge of the spill at or outside its perimeter. Path 36 bypasses the switching means 34 in the event use of the switching means 34 is not desired.

The images viewed on monitors 14 and 18 can be recorded with a VCR unit 15 which stores them for future viewing. Recording the images on tape serves two purposes. First, it allows replay of the observations, providing information for the personnel charged with cleanup of the spill and second, it provides documentation of the work accomplished for later review. Moreover, an audio amplification system to amplify sound from a microphone used in documentation on the VCR tape or second sound recording system is also beneficial to the spill clean-up process. If recording is not required, VCR 15 can be bypassed by paths 37 and 38, indicated by dotted lines on FIG. 2. Furthermore, if recording is desired, paths 37 and 38 may be used as secondary information paths while the VCR is in use.

Clearly, the general object of the present invention to provide an improved system for distinguishing the spill from the nonspill area has been met. Moreover, the object of the present invention to provide a real-time fluorescent video imaging system which may be used in the daylight has also been met. Also, the object of the present invention to provide a system which avoids influence from the source of excitation light in the reception of the emission signals has been met as has been the object to provide an excitation source which operates at wavelengths providing optimized fluorescent emissions of most insulating liquids and a detector which receives the fluorescent emission signals at their optimized wavelengths. Furthermore, the object to provide a system to better map the boundaries of a spill occurring on surfaces such as asphalt, concrete, metal, grass and dirt and wet surfaces by providing a means for distinguishing and enhancing the fluorescent emissions of the spill contents has been met. Finally, the object to have at least two detectors, a first for viewing fluorescent emissions and a second for viewing the normal video image and means to switch between their transmissions at a monitor has been met.

While the present invention has been shown and described in what is presently conceived to be the most practical and preferred embodiment of the invention, it will become apparent to those of ordinary skill in the art that many modifications thereof may be made within the scope of the invention, which scope is to be accorded the broadest interpretation of the claims so as to encompass all equivalent structures.

What is claimed is:

1. A portable real-time fluorescence imaging system for detecting the presence and boundaries on-site of a spill of a fluorescing species, said system comprising:
   hand carried excitation means positionable near the spill for exciting fluorescent emissions of said fluorescing species;
   pulse means for causing said excitation means to periodically excite said fluorescent emissions with pulsed periods of fluorescent excitation;
   image intensification means for intensifying said periodically excited fluorescent emissions;
   hand carried first detection means fixedly positionable for detecting said intensified fluorescent emissions and generating a first detection signal representing said detected fluorescent emissions;
   control means for controlling said intensification means to intensity only during said pulsed periods of fluorescent excitation so that a majority of any interfering emissions are not detected by said first detection means;
   display means for receiving said first detection signal and for generating from said first detection signal a real-time fluorescent video image of the presence and boundaries of said spill.

2. A portable real-time fluorescence imaging system for detecting the presence and boundaries on-site of a spill of a fluorescing species, said system comprising:
   hand carried excitation means positionable near a spill for exciting fluorescent emissions of said fluorescing species;
   trigger pulse means for enabling said excitation means to periodically excite said fluorescent emissions;
   image intensification means for intensifying said periodically excited fluorescent emissions;
   hand carried first detection means fixedly positionable for detecting said intensified fluorescent emissions and for generating a first detection signal representing said detected fluorescent emissions;
   display means for receiving said first detection signal and for generating from said first detection signal a real-time fluorescent video image of said detected fluorescent emissions; and
   synchronization means for synchronizing said trigger pulse means and said image intensification means so that a majority of any interfering emissions are not detected by said first detection means.

3. A system as recited in claim 1 or 2 wherein said fluorescing species is an insulating liquid.

4. A system as recited in claim 1 or 2 wherein said fluorescing species contains PCBs.

5. A system as recited in claim 1 or 2 wherein said excitation means is a mercury lamp providing excitation within wavelengths of between approximately 190 nm to 350 nm for exciting said fluorescent emissions.

6. A system as recited in claim 1 or 2 wherein said excitation means is a xenon lamp providing excitation within wavelengths of between approximately 190 nm to 350 nm for exciting said fluorescent emissions.

7. A system as recited in claim 1 or 2 wherein said first detection means is sensitive to wavelengths between approximately 325 nm and 450 nm.

8. A system as recited in claim 1 or 2 wherein:
said display means is also for receiving a second detection signal representing a normal image of said spill, for generating a real-time normal video image of said spill, and for allowing correlation of said fluorescent video image with said normal video image for mapping the boundaries of said spill;
said system further comprising:
second detection means positionable for detecting said normal image of said spill and for generating said second detection signal.

9. A system as recited in claim 1 or 2 wherein:
said display means is also for receiving a second detection signal representing a normal image of said spill, for generating a real-time normal video image of said spill, and for allowing correlation of said fluorescent video image with said normal video image for mapping the boundaries of said spill;
said system further comprising:
second detection means positionable for detecting said normal image of said spill and for generating said second detection signal; and
switching means for allowing a viewer of said display means to view on command said fluorescent and normal video images simultaneously or back to back for said correlation of said fluorescent video image with said normal video image.

10. A system as recited in claim 1 or 2 wherein said excitation means is a light bulb providing excitation within wavelengths of between approximately 190 nm to 350 nm for exciting said fluorescent emissions.

11. A system as recited in claim 10 wherein said light bulb has:
a roughened surface except for an opening through which light passes; and
an aluminized coating over said roughened surface.

12. The system as recited in claim 11 wherein said opening is approximately 1.27 cm in diameter.

13. A method for providing real-time on-site fluorescence imaging for detecting the presence and boundaries of a spill of a fluorescing species, said method comprising the steps of:
positioning a hand carried excitation source and a hand carried detector near said spill;
with said hand carried excitation source, periodically exciting fluorescent emissions of said fluorescing species with pulsed periods of fluorescent excitation;
intensifying said fluorescent emissions only during said pulsed periods of fluorescent excitation so that a majority of any interfering emissions will not be detected;
with said hand carried detector, detecting said intensified fluorescent emissions;
displaying a real-time fluorescent video image of said detected fluorescent emissions.

14. A method as recited in claim 13 wherein said fluorescing species is an insulating liquid.

15. A method as recited in claim 13 wherein said fluorescing species contains PCBs.

16. A method as recited in claim 13 wherein:
said displaying step includes displaying a real-time normal video image of said spill and allowing correlation of said fluorescent video image with said normal video image for mapping the boundaries of said spill;
said method further comprising the steps of:
detecting said normal image of said spill.

17. A method for providing real-time on-site fluorescence imaging for detecting the presence and boundaries of a spill of a fluorescing species, said method comprising the steps of:
periodically exciting fluorescent emissions of said fluorescing species with pulsed periods of fluorescent excitation;
intensifying said fluorescent emissions only during said pulsed periods of fluorescent excitation so that a majority of any interfering emissions will not be detected;
detecting said intensified fluorescent emissions;
displaying a real-time fluorescent video image of said detected fluorescent emissions; and
applying an absorbent powder to the area of said spill, said absorbent powder absorbing said fluorescing species from the underlying ground to concentrate said fluorescing species at the ground's surface for increased excitation of said fluorescent emissions, said absorbent powder also reflecting some of said fluorescent excitation onto said spill so as to excite said fluorescent emissions even further.

18. A method as recited in claim 17 wherein said powder comprises $CaSO_4$.

* * * * *